(12) United States Patent
Hares et al.

(10) Patent No.: US 12,150,721 B2
(45) Date of Patent: Nov. 26, 2024

(54) CONTROLLING A SURGICAL INSTRUMENT

(71) Applicant: CMR SURGICAL LIMITED, Cambridge (GB)

(72) Inventors: Luke David Ronald Hares, Cambridge (GB); Gordon Thomas Deane, Cambridge (GB); Edward James Wildin Tucker, Cambridge (GB); Graham John Veitch, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 838 days.

(21) Appl. No.: 17/105,703

(22) Filed: Nov. 27, 2020

(65) Prior Publication Data

US 2021/0161606 A1   Jun. 3, 2021

(30) Foreign Application Priority Data

Nov. 29, 2019   (GB) .................................... 1917491

(51) Int. Cl.
*A61B 34/00* (2016.01)
*A61B 17/04* (2006.01)
(Continued)

(52) U.S. Cl.
CPC .......... *A61B 34/30* (2016.02); *A61B 17/0469* (2013.01); *A61B 17/2909* (2013.01); (Continued)

(58) Field of Classification Search
CPC . A61B 34/30; A61B 17/0469; A61B 17/2909; A61B 2017/00039;
(Continued)

(56) References Cited

U.S. PATENT DOCUMENTS 9,084,623 B2 *   7/2015   Gomez .................. B25J 9/1679
10,575,909 B2 *  3/2020   Robinson ............... A61B 34/35
(Continued)

FOREIGN PATENT DOCUMENTS

JP   2015502198 A   1/2015
JP   2019505260 A   2/2019
(Continued)

OTHER PUBLICATIONS

Australian Examination Report No. 2 from corresponding Australian Application No. 2020392895 dated Sep. 28, 2023.
(Continued)

*Primary Examiner* — Ian Jen
(74) *Attorney, Agent, or Firm* — Lando & Anastasi, LLP (57) ABSTRACT

A control system for controlling manipulation of a surgical instrument in response to manipulation of a remote surgeon input device at a remote surgeon's console, the surgical instrument being supported by a surgical robot arm, the surgical instrument comprising an end effector connected to a distal end of a shaft by an articulated coupling, the articulated coupling comprising one or more joints enabling the end effector to adopt a range of attitudes relative to the distal end of the shaft, the control system configured to: receive a command from an input actuated by a user to straighten the surgical instrument; and in response to the received command, to command driving forces to be applied to joint(s) of the articulated coupling to drive the instrument to adopt a predetermined configuration in which the profile of the end effector is most closely aligned with the profile of the distal end of the shaft.

19 Claims, 8 Drawing Sheets

(51) Int. Cl.
  *A61B 17/29* (2006.01)
  *A61B 34/30* (2016.01)
  *B25J 9/16* (2006.01)
  *A61B 17/00* (2006.01)
(52) U.S. Cl.
  CPC ....... *B25J 9/16* (2013.01); *A61B 2017/00039* (2013.01); *A61B 2017/00199* (2013.01); *A61B 2017/00203* (2013.01); *A61B 2017/00207* (2013.01); *A61B 2017/00212* (2013.01); *A61B 2017/00477* (2013.01); *A61B 2017/2908* (2013.01)
(58) Field of Classification Search
  CPC ........... A61B 2017/00199; A61B 2017/00203; A61B 2017/00207; A61B 2017/00212; A61B 2017/00477; A61B 2017/2908
  See application file for complete search history.

(56) References Cited

U.S. PATENT DOCUMENTS

| | | | |
|---|---|---|---|
| 11,589,771 B2* | 2/2023 | Johnson | A61B 90/96 |
| 11,596,488 B2* | 3/2023 | Gomez | A61B 50/20 |
| 11,622,823 B2* | 4/2023 | Vakharia | A61B 34/30 |
| | | | 700/257 |
| 11,659,978 B2* | 5/2023 | Larkin | A61B 5/0086 |
| | | | 600/114 |
| 2007/0013336 A1* | 1/2007 | Nowlin | A61B 34/37 |
| | | | 318/568.21 |
| 2011/0040305 A1* | 2/2011 | Gomez | A61B 34/74 |
| | | | 606/130 |
| 2012/0059392 A1 | 3/2012 | Diolaiti | |
| 2013/0231680 A1 | 9/2013 | Diolaiti et al. | |
| 2016/0270867 A1 | 9/2016 | Scholan | |
| 2016/0346930 A1 | 12/2016 | Hares | |
| 2017/0165012 A1 | 6/2017 | Chaplin et al. | |
| 2018/0008359 A1* | 1/2018 | Randle | A61B 34/32 |
| 2018/0140371 A1 | 5/2018 | Hares et al. | |
| 2018/0147017 A1 | 5/2018 | Marshall et al. | |
| 2018/0364891 A1 | 12/2018 | Hares | |

FOREIGN PATENT DOCUMENTS

| | | |
|---|---|---|
| WO | 2018020252 A2 | 2/2018 |
| WO | 2018162921 A1 | 9/2018 |
| WO | 2021079114 A1 | 4/2021 |

OTHER PUBLICATIONS

United Kingdom Search Report from corresponding United Kingdom Application No. GB191749.1 dated Jun. 3, 2020.

Notification of Transmittal of the International Search Report and the Written Opinion of the International Searching Authority from corresponding PCT/GB2020/053040 dated Mar. 10, 2021.

* cited by examiner

CONTROLLING A SURGICAL INSTRUMENT

CROSS-REFERENCE TO RELATED APPLICATION

This application claims the benefit under 35 U.S.C. § 119 of United Kingdom Patent Application No. 1917491.1 filed on Nov. 29, 2019 which is hereby incorporated herein by reference in its entirety for all purposes.

BACKGROUND

Figure 1:
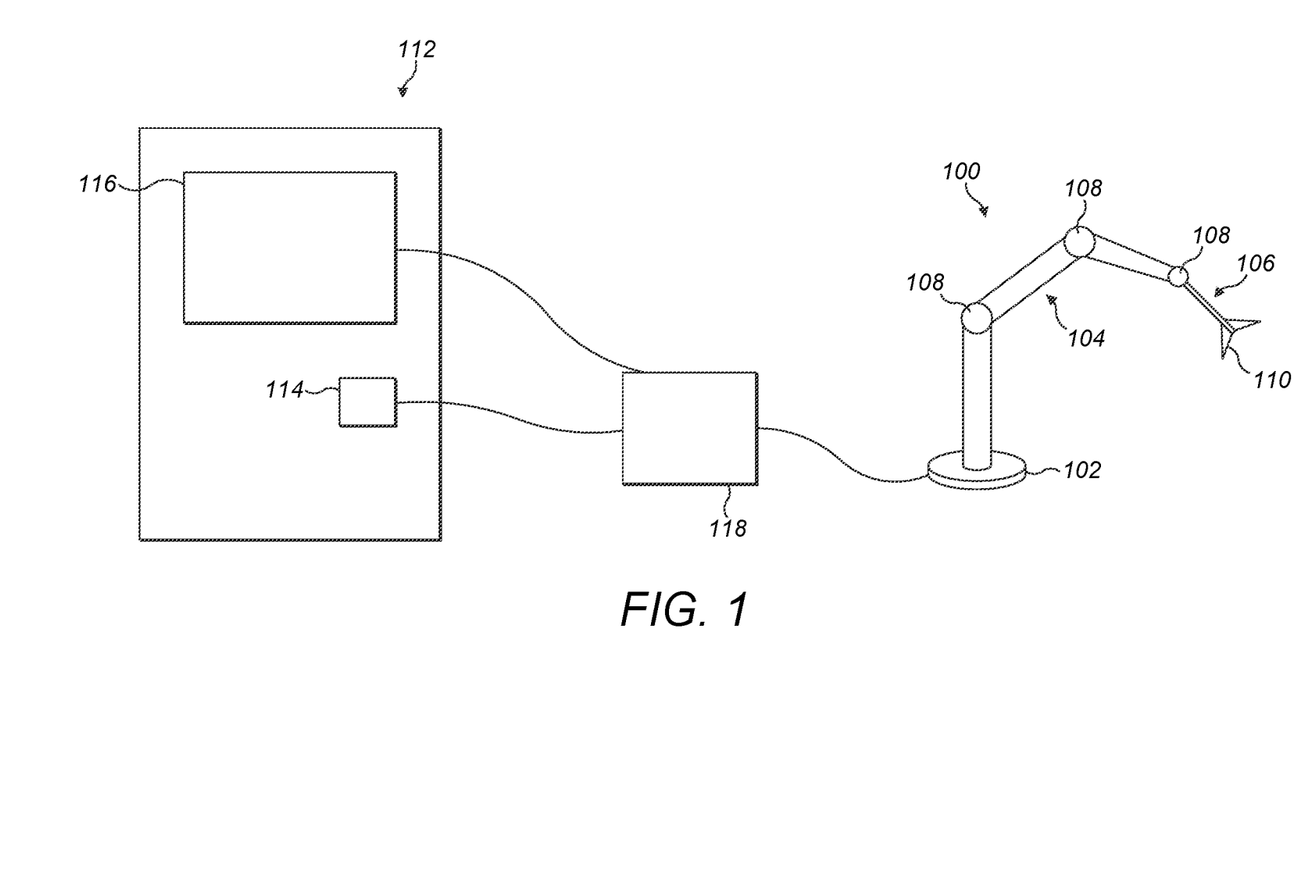
FIG. 1 illustrates a surgical robot system for performing a surgical procedure.

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. The surgical instrument comprises a shaft connected to a distal end effector 110 by a jointed articulation. The end effector engages in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly.

There are times when the surgical instrument 106 and/or the robot arm 104 get into an awkward configuration which the surgeon wants to change. For example, when suturing, the surgical instrument is rotated about its longitudinal axis by means of the final roll joint on the robot arm rotating about its rotation axis. In doing so, the arm roll joint may reach a joint limit. In order to continue suturing, the surgeon first performs an unrolling motion of the surgeon input device several times in order to cause the arm roll joint to unroll and hence the instrument to unroll. This unrolling motion can be time consuming and tiring on the surgeon's wrist, particularly if it needs to be performed regularly during a suturing operation. It may also not be apparent to the surgeon when the roll joint has been fully unrolled. There is thus a need to aid the surgeon in handling such situations.

SUMMARY OF THE INVENTION

According to an aspect of the invention, there is provided a control system for controlling manipulation of a surgical instrument in response to manipulation of a remote surgeon input device at a remote surgeon's console, the surgical instrument being supported by a surgical robot arm, the surgical instrument comprising an end effector connected to a distal end of a shaft by an articulated coupling, the articulated coupling comprising one or more joints enabling the end effector to adopt a range of attitudes relative to the distal end of the shaft, the control system configured to: receive a command from an input actuated by a user to straighten the surgical instrument; and in response to the received command, to command driving forces to be applied to joint(s) of the articulated coupling to drive the instrument to adopt a predetermined configuration in which the profile of the end effector is most closely aligned with the profile of the distal end of the shaft.

In the predetermined configuration, each joint of the articulated coupling may be at the centre of its range of motion.

The articulated coupling may comprise a pitch joint and two yaw joints.

The end effector may comprise a pair of opposable end effector elements separated by an opening angle, wherein in the predetermined configuration, the opening angle is minimised.

The surgical robot arm may comprise a series of links between a base and an attachment for the surgical instrument, the links being interspersed by joints, the control system being configured to, in response to the received command, additionally command driving forces to be applied to one or more joints of the surgical robot arm to drive the surgical robot arm to adopt a predetermined arm configuration.

The surgical robot arm may comprise a terminal joint adjacent to the attachment for the surgical instrument, that terminal joint being a roll joint, wherein in response to the received command, the control system is configured to command a driving force to be applied to the roll joint to drive the roll joint to the centre of its range of motion.

In the predetermined arm configuration, the attachment for the surgical instrument may be oriented such that the surgical instrument can be attached and/or removed vertically from the attachment for the surgical instrument when the surgical robot arm is on a horizontal surface.

The predetermined arm configuration may match a configuration of the robot arm whilst the surgical instrument was being attached to the attachment for the surgical instrument.

The control system may be configured to, on receiving the command from the input, wait for a predetermined time before responding by commanding driving forces to be applied to the articulated coupling and/or robot arm joints.

The control system may be configured to, on receiving the command from the input, measure the current configuration of the surgical instrument, and only command driving forces to be applied to joint(s) of the articulated coupling if the current configuration of the surgical instrument differs from the predetermined configuration by greater than an instrument tolerance value.

The control system may be configured to, on receiving the command from the input, measure the current configuration of the robot arm, and only command driving forces to be applied to joint(s) of the surgical robot arm if the current configuration of the robot arm differs from the predetermined arm configuration by greater than an arm tolerance value.

The input may be part of the remote surgeon's console.

The input may be located on a hand controller of the remote surgeon's console, the input able to be actuated by motion of the user's hand.

The input may be a voice sensor able to be actuated by the user's voice.

The input may be a combined input located on two hand controllers of the remote surgeon's console, the combined input able to be actuated by motion of both of the user's hands.

The control system may be configured to, on receiving the command: determine if the surgeon has active control of the surgical instrument; and only if the surgeon has active control of the surgical instrument, respond to the received command by commanding driving forces to be applied to joint(s) of the articulated coupling.

The input may be on the surgical robot arm.

The control system may be configured to, on receiving the command: determine if an instrument change mode has been enabled; and only if the instrument change mode has been enabled, respond to the received command by commanding driving forces to be applied to joint(s) of the articulated coupling.

The control system may be configured to only command driving forces to be applied to joint(s) of the articulated coupling and/or robot arm joints whilst the input is being actuated by the user.

The control system may be configured to: receive the command from the input on the surgical robot arm; receive another command from an input on the remote surgeon input device, the other command to manipulate the surgical instrument; and override the other command with the command from the input on the surgical robot arm.

BRIEF DESCRIPTION OF THE FIGURES

The present invention will now be described by way of example with reference to the accompanying drawings. In the drawings.

DETAILED DESCRIPTION

The following describes controlling a surgical robot arm and a surgical robotic instrument from a remote surgeon console and/or the surgical robot arm. The arm, instrument and console form part of a surgical robotic system of the type illustrated in FIG. 1.

The surgical instrument is supported by the robot arm. The robot arm is itself supported by a base. During surgery, the base is secured to part of the operating theatre, for example the floor, ceiling, cart or patient bed. The robot arm remains at all times external to the patient. The robot arm comprises a series of arm links interspersed with joints. These joints may be revolute joints. The end of the robot arm distal to the base can be articulated relative to the base by movement of one or more of the joints. The surgical instrument attaches to a drive assembly at the distal end of the robot arm. This attachment point is external to the patient.

The surgical instrument has an elongate profile, with a shaft spanning between its proximal end which attaches to the robot arm and its distal end which accesses the surgical site within the patient body. The proximal end of the surgical instrument and the instrument shaft may be rigid with respect to each other and rigid with respect to the distal end of the robot arm when attached to it. An incision is made into the patient body, through which a port is inserted. The surgical instrument may penetrate the patient body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface each engage a respective individual drive assembly interface element of the drive assembly. The instrument interface is releasably engageable with the drive assembly. The instrument can be detached from the robot arm manually without requiring any tools. This enables the instrument to be detached from the drive assembly quickly and another instrument attached during an operation.

Figure 2A:
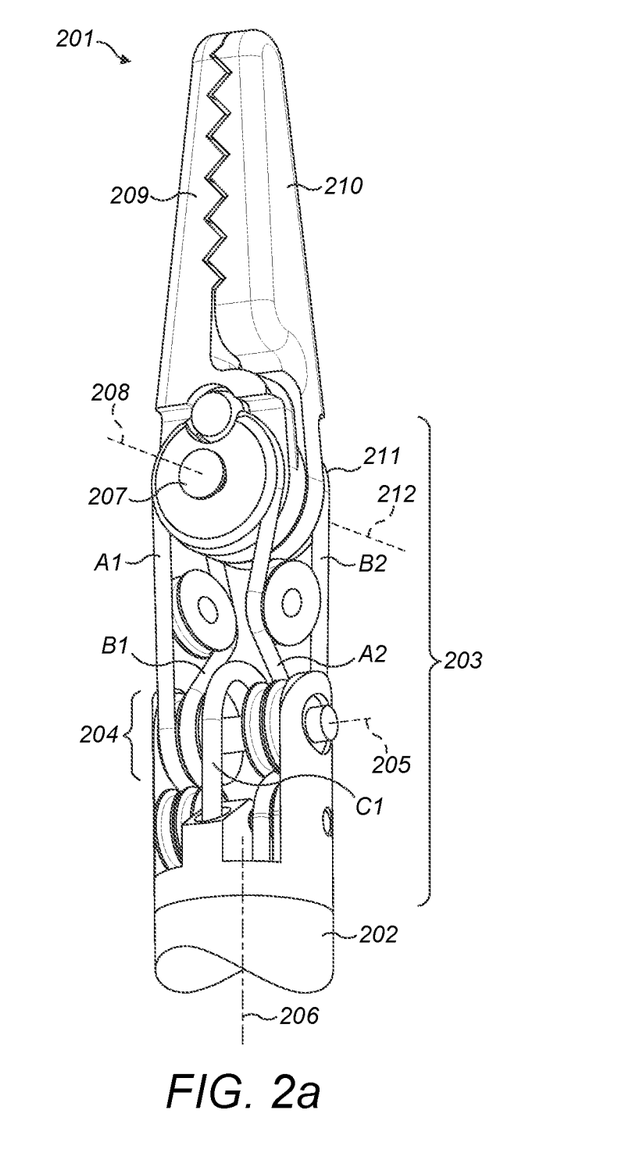
FIGS. 2a and 2b illustrate the distal end of an exemplary surgical instrument.
Figure 2B:
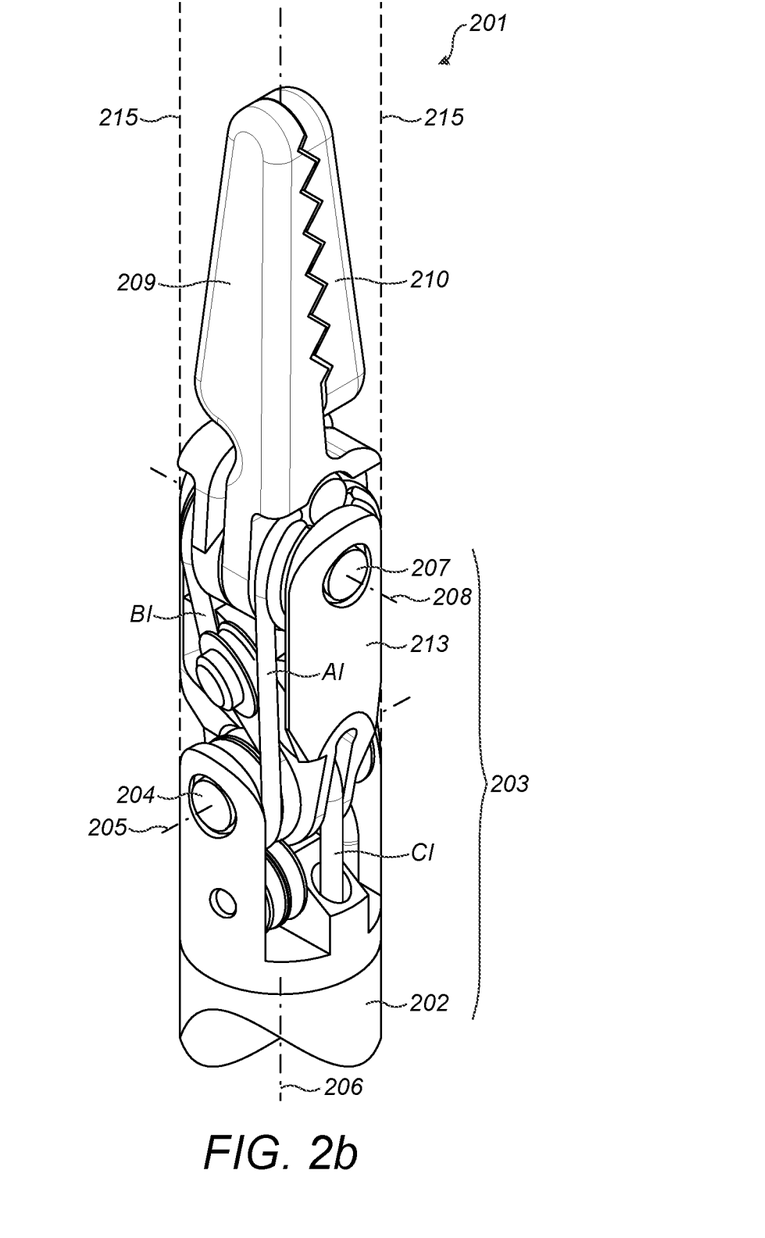

At the distal end of the surgical instrument, the distal end of the shaft is connected to an end effector by an articulated coupling. The end effector engages in a surgical procedure at the surgical site. FIGS. 2a and 2b illustrate the distal end of an exemplary instrument which has a pair of jaws as the end effector 201. The shaft 202 is connected to the end effector 201 by articulated coupling 203. The articulated coupling 203 comprises several joints. These joints enable the pose of the end effector to be altered relative to the direction of the instrument shaft. Although not shown in FIGS. 2a and 2b, the end effector may also comprise joint(s). In the example of FIGS. 2a and 2b, the articulated coupling 203 comprises a pitch joint 204. The pitch joint 204 rotates about pitch axis 205, which is perpendicular to the longitudinal axis 206 of the shaft 202. The pitch joint 204 permits a supporting body 213 (described below) and hence the end effector 201 to rotate about the pitch axis 205 relative to the shaft. In the example of FIGS. 2a and 2b, the articulated coupling also comprises a first yaw joint 207 and a second yaw joint 211. First yaw joint 207 rotates about first yaw axis 208. Second yaw joint 211 rotates about second yaw axis 212. Both yaw axes 208 and 212 are perpendicular to pitch axis 205. Yaw axes 208 and 212 may be parallel. Yaw axes 208 and 212 may be collinear. The articulated coupling 203 comprises a supporting body 213. At one end, the supporting body 213 is connected to the shaft 202 by pitch joint 204. At its other end, the supporting body 213 is connected to the end effector 201 by the yaw joints 207 and 211. This supporting body is omitted from FIG. 2a for ease of illustration so as to enable the other structure of the articulated coupling to be more easily seen. The end effector 201 shown comprises two end effector elements 209, 210. Alternatively, the end effector may have a single end effector element. The end effector elements 209, 210 shown in FIGS. 2a and 2b are opposing jaws.

However, the end effector elements may be any type of opposing end effector elements. The first yaw joint 207 is fast with the first end effector element 209 and permits the first end effector element 209 to rotate about the first yaw axis 208 relative to the supporting body 213 and the pitch joint 204. The second yaw joint 211 is fast with the second end effector element 210 and permits the second end effector element 210 to rotate about the second yaw axis 212 relative to the supporting body 213 and the pitch joint 204. In FIG. 2a, the end effector elements 209, 210 are shown in a closed configuration in which the jaws abut. Generally speaking, the end effector elements 209, 210 are separated by an opening angle.

The joints illustrated in FIGS. 2a and 2b are driven by pairs of driving elements. The driving elements are elongate. They are flexible transverse to their longitudinal extent. They resist compression and tension forces along their longitudinal extent. Each pair of driving elements is secured at the other end of the instrument shaft to a respective instrument interface element of the instrument interface. Thus, the robot arm transfers drive to the end effector as follows: movement of a drive assembly interface element moves an instrument interface element which moves a driving element which moves one or more joints of the articulation and/or end effector which moves the end effector. The driving elements may be cables. The driving elements may comprise flexible portions and a rigid portion. Flexible portions engage the components of the instrument interface and the articulated coupling, and the rigid portion extends through all or part of the instrument shaft. For example, the flexible portion may be a cable, and the rigid portion may be a spoke. Other rigid portion(s) may be in the instrument interface or articulated coupling of the instrument. For example, rack and pinions may be in the instrument interface or articulated coupling of the instrument.

FIGS. 2a and 2b illustrate a first pair of driving elements A1, A2 which are constrained to move around the first yaw joint 207. Driving elements A1, A2 drive rotation of the first end effector element 209 about the first yaw axis 208. FIGS. 2a and 2b illustrate a second pair of driving elements B1, B2 which are constrained to move around the second yaw joint 211. Driving elements B1, B2 drive rotation of the second end effector element 210 about the second yaw axis 212. FIGS. 2a and 2b also illustrate a third pair of driving elements C1, C2 which are constrained to move around pitch joint 204. Driving elements C1, C2 drive rotation of the end effector 201 about the pitch axis 205. The end effector 201 can be rotated about the pitch axis 205 by applying tension to driving elements C1 and/or C2. The pitch joint 204 and yaw joints 207, 211 are independently driven by their respective driving elements.

The end effector elements 209 and 210 are independently rotatable. The end effector elements can be rotated in opposing rotational directions. For example, the end effector elements can be rotated in opposing rotational directions towards each other by applying tension to driving elements A2 and B1. The end effector elements can be rotated in opposing rotational directions away from each other by applying tension to driving elements A1 and B2. Both end effector elements can be rotated in the same rotational direction, by applying tension to driving elements A1 and B1 or alternatively A2 and B2. This causes the end effector elements to yaw about the pivot axes 208 and 212. Alternatively, one end effector element can be rotated (in either rotational direction) whilst the other end effector element is maintained in position, by applying tension to only one of driving elements A1, A2, B1, B2.

Figure 3:
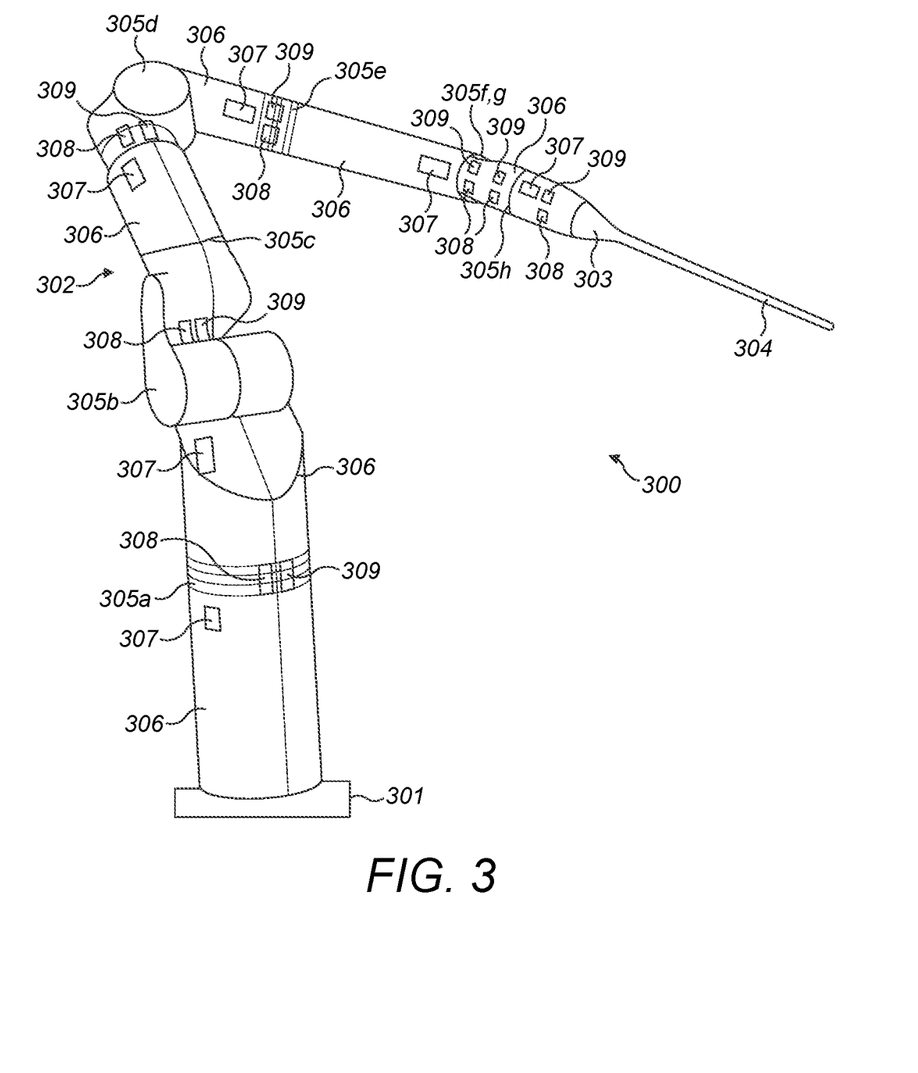
FIG. 3 illustrates a robot.

FIG. 3 illustrates an example robot 300. The robot comprises a base 301 which is fixed in place when a surgical procedure is being performed. Suitably, the base 301 is mounted to a chassis. That chassis may be a cart, for example a bedside cart for mounting the robot at bed height. Alternatively, the chassis may be a ceiling mounted device, or a bed mounted device.

A robot arm 302 extends from the base 301 of the robot to an attachment 303 for a surgical instrument 304. The arm is flexible. It is articulated by means of multiple flexible joints 305 along its length. In between the joints are rigid arm links 306. The arm in FIG. 3 has eight joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). In the example of FIG. 3: joints 305a, 305c, 305e and 305h are roll joints; joints 305b, 305d and 305f are pitch joints; and joint 305g is a yaw joint. Pitch joint 305f and yaw joint 305g have intersecting axes of rotation. The order of the joints from the base 301 to the attachment 303 are thus: roll, pitch, roll, pitch, roll, pitch, yaw, roll. However, the arm could be jointed differently. For example, the arm may have fewer than eight or more than eight joints. The arm may include joints that permit motion other than rotation between respective sides of the joint, for example a telescopic joint. The robot comprises a set of drivers 307, each driver 307 drives one or more of the joints 305.

The attachment 303 enables the surgical instrument 304 to be releasably attached to the distal end of the robot arm. The surgical instrument may be configured to extend linearly parallel with the rotation axis of the terminal joint 305h of the arm. For example, the surgical instrument may extend along an axis coincident with the rotation axis of the terminal joint of the arm.

The robot arm comprises a series of sensors 308, 309. These sensors comprise, for each joint, a position sensor 308 for sensing the position of the joint, and a torque sensor 309 for sensing the applied torque about the joint's rotation axis. One or both of the position and torque sensors for a joint may be integrated with the motor for that joint. The outputs of the sensors are passed to the control system 118.

Figure 4A:
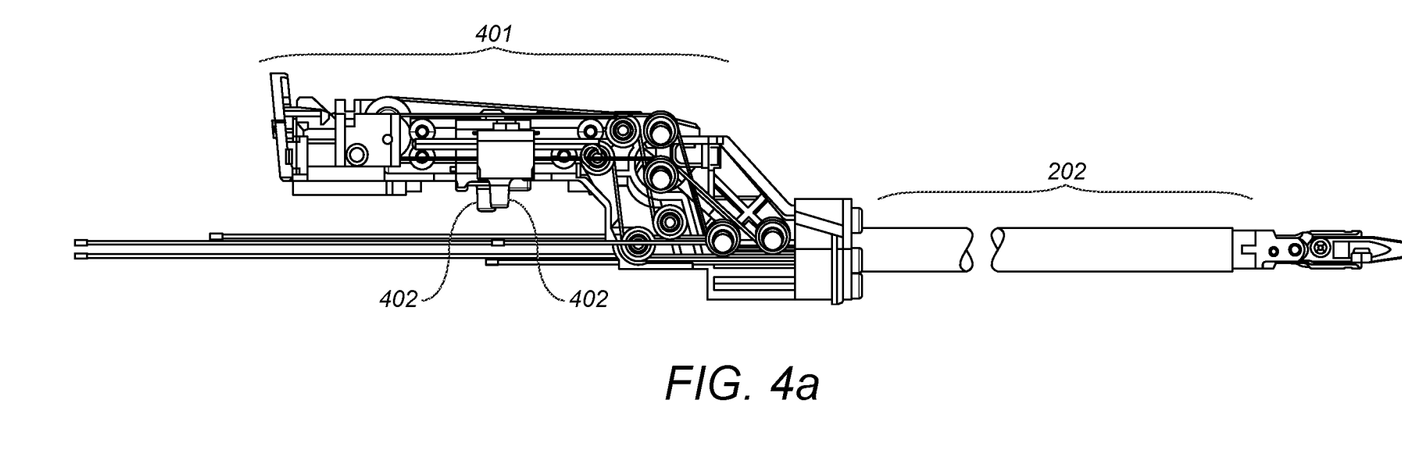
FIGS. 4a, 4b and 4c illustrate the interface between a robot arm and a surgical instrument.

FIGS. 4a, 4b and 4c illustrate the interface between the distal end of the robot arm and the proximal end of the instrument. FIG. 4a illustrates the instrument interface 401. The instrument interface 401 is rigidly attached to the instrument shaft 202. The instrument shaft 202 does not rotate or otherwise move relative to the instrument interface 401. The instrument interface comprises instrument interface elements 402, each of which is secured to a driving element. That driving element extends down shaft 202 for driving a joint of articulation 203. The instrument interface elements 402 are exposed so as to be capable of interfacing with the robot arm.

Figure 4B:
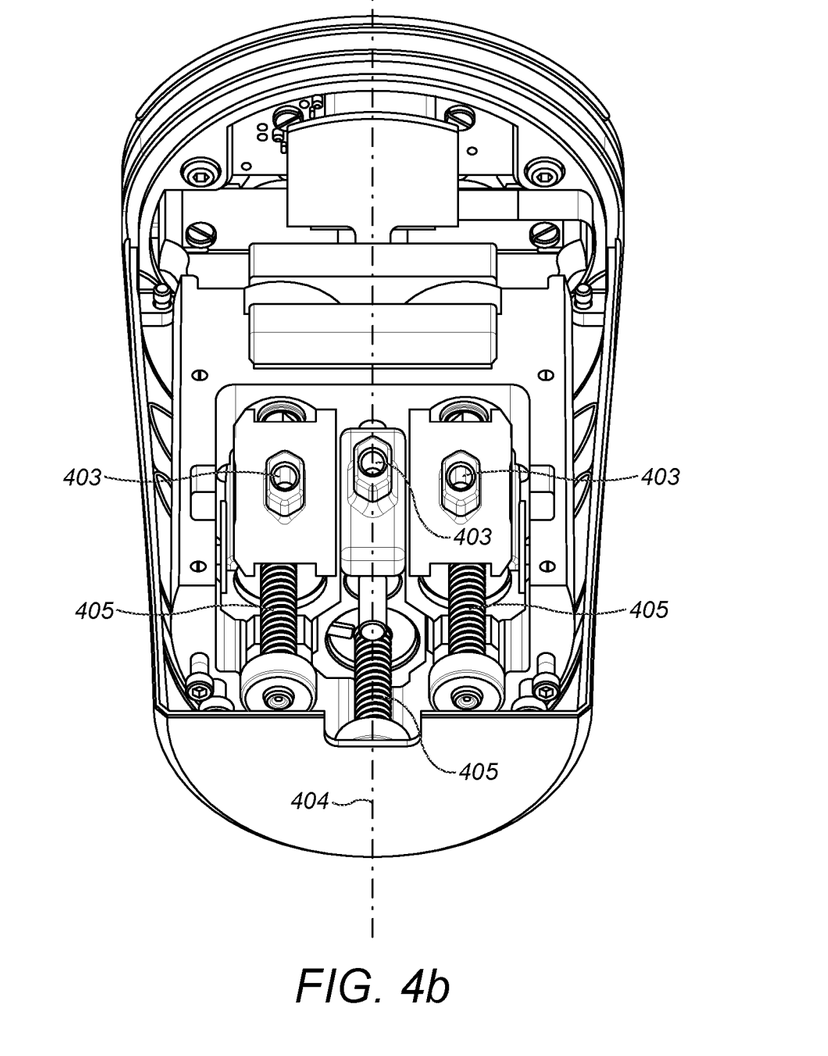
Figure 4C:
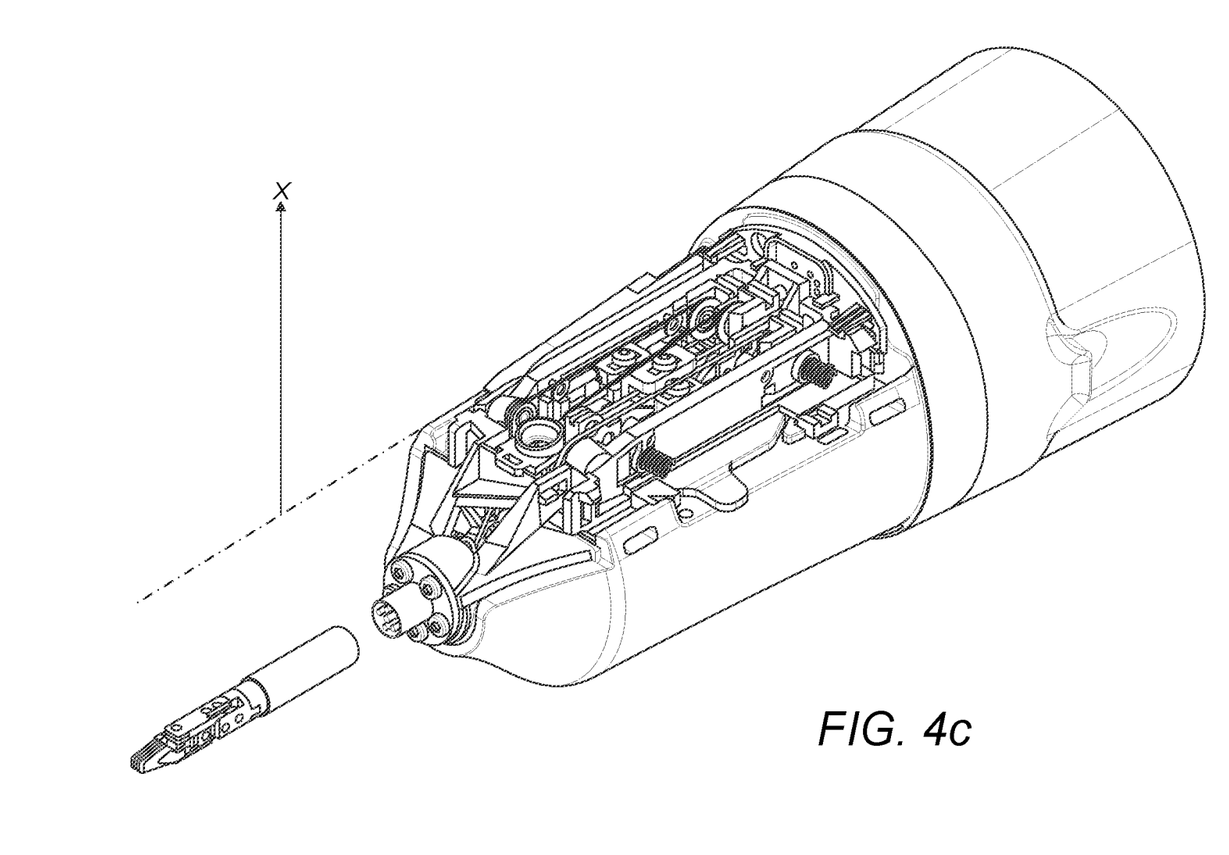

FIG. 4b illustrates the drive assembly interface at the distal end of the robot arm. Drive assembly interface elements 403 each have a complimentary shape to the instrument interface elements 402. Thus, drive assembly interface elements 403 are shaped so as to receive instrument interface elements 402. The drive assembly interface elements 403 are each driveable along a direction parallel to the longitudinal axis 404 of the distal end of the robot arm along lead screws 405. The instrument interface is lowered into the drive assembly causing the instrument interface elements 402 to engage in the drive assembly interface elements 403. FIG. 4c illustrates the instrument interface engaged in the drive assembly interface. The robot arm may now drive movement of the articulation 203 by driving movement of the drive assembly interface elements 403 along the lead screws 405.

The surgeon console comprises one or more surgeon input devices. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

Figure 5:
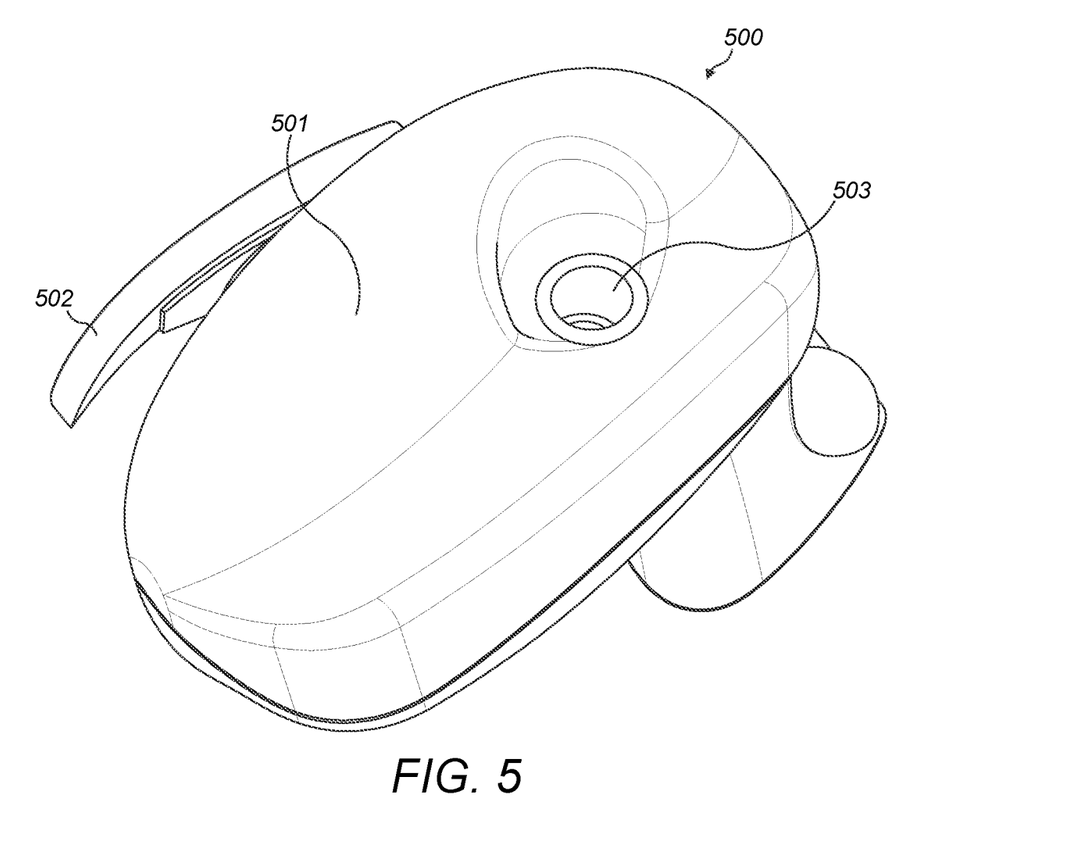
FIG. 5 illustrates a surgeon input device.

FIG. 5 illustrates an exemplary hand controller 500. The hand controller is connected to the surgeon console, for example by a gimbal arrangement (not shown). This enables the hand controller to be moved with three degrees of translational freedom with respect to the surgeon console. Such movement may be used to command corresponding movement of the end effector 201 of the instrument. The hand controller shown is intended to be held by a right hand. A mirror image hand controller could be held by a left hand. The hand controller comprises a body 501 suitable for being gripped by a hand. The hand controller may comprise additional inputs, for example buttons, switches, levers, slide inputs or capacitive sensor inputs such as track pads 503. The hand controller of FIG. 5 comprises a trigger 502. The trigger 502 is movable relative to the body 501. In the hand controller shown, the trigger 502 is rotatable relative to the body 501. Alternatively, or in addition, the trigger could translate linearly relative to the body 501. Movement of the trigger 502 relative to the body 501 may be used to command opening and closing of the end effector elements 209, 210 of the instrument. The hand controller may comprise two triggers, each trigger for independently controlling a single different one of the end effector elements 209, 210.

A control system connects the surgeon console to the surgical robot. The control system comprises a processor and a memory. The memory stores, in a non-transient way, software code that can be executed by the processor to cause the processor to control the surgeon console and robot arm and instrument in the manner described herein. The control system receives the inputs from the surgeon input device(s) and converts these to control signals to move the joints of the robot arm and/or the joint(s) of the articulated coupling and/or the joint(s) of the end effector. The control system sends these control signals to the robot arm, where the corresponding joints are driven accordingly. Manipulation of the surgical instrument is thereby controlled by the control system in response to manipulation of the surgeon input device.

As will be described in more detail below, the control system also receives a further input. The control system responds to this further input in the same manner as above, by converting it to control signals to move the joints of the robot arm and/or the joint(s) of the articulated coupling and/or the joint(s) of the end effector. The control system sends these control signals to the robot arm, where the corresponding joints are driven accordingly. Manipulation of the surgical instrument and robot arm is thereby also controlled by the control system in response to the further input.

There are times during an operation when the surgeon may want to straighten the instrument. For example, when the surgical instrument is being removed from the body it passes through the port. The distal end of the surgical instrument is straightened in order for it to fit through the port. To do this, the surgeon can manually manipulate the surgeon input device to rotate each joint of the articulated coupling in order to straighten the instrument. Ideally, the distal end of the instrument is visible in the video feed from the endoscope inside the body in order for the surgeon to have visual confirmation that the distal end of the surgical instrument is in the straightened position prior to it having reached the port.

As another example, when suturing, a rotation of the surgical instrument is repetitively commanded. This may be achieved either by rotating a roll joint of the shaft of the instrument or by rotating the final roll joint 305h of the robot arm. This can lead to the roll joint reaching a joint limit. The surgical instrument is straightened by unrolling the roll joint, in order for it to be capable of being used for suturing again. To do this, the surgeon can manually manipulate the surgeon input device to unroll the instrument. It may not be apparent when the instrument has been fully unrolled. In both the scenarios described above, the surgeon remains in control of the instrument. The surgeon retaining control of the surgical instrument in these scenarios is important for safety reasons.

Figure 6:
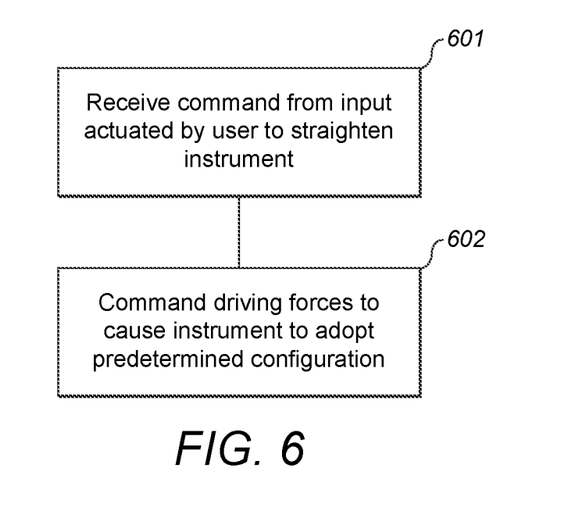
FIG. 6 is a flowchart of a method of controlling manipulation of a surgical instrument.

FIG. 6 describes a method of controlling a surgical instrument to be straightened in response to a command from an input actuated by a user.

At step 601, the control system receives a command from an input actuated by a user to straighten the surgical instrument. The input may be part of the surgeon's console 112. For example, the input may be on the hand controller 500 configured to be actuated by motion of the user's hand. For example, the input may be a button, switch or slider on the hand controller. The input may be a combined input from two hand controllers configured to be actuated by motion of both of the user's hands. For example, the input may be a concurrent button press on both of the hand controllers. The input may be a voice sensor on the surgeon's console 112 actuated by the user's voice. For the described exemplary inputs on the surgeon's console, the surgeon is the user.

Alternatively, or additionally, the input may be on the surgical robot arm. Alternatively, or additionally, the input may be on a support structure to which the surgical robot arm is mounted, for example a cart or bed. For example, the input may be a button, switch, slider, or touch pad located on the external casing of the robot arm or support structure. For the described exemplary inputs on the robot arm or support structure, a member of bedside staff is the user.

The system may comprise two or more inputs which can be actuated by a user to straighten the surgical instrument. For example, one of the inputs may be located on the surgeon's console 112, and another of the inputs may be located on the robot arm.

At step 602, the control system responds to the received command by commanding driving forces to be applied to one or more joints of the articulated coupling and/or the instrument shaft to drive the instrument to adopt a predetermined configuration.

The end effector can adopt a range of attitudes relative to the profile of the distal end of the shaft of the instrument, each dependent on the rotation angles of the joints of the articulated coupling 203 about their rotation axes. The predetermined configuration of step 602 may be one in which the profile of the end effector is most closely aligned with the profile of the distal end of the shaft. In other words, of the range of attitudes that the end effector may adopt relative to the profile of the distal end of the shaft, the predetermined configuration is the one in which the end effector is most closely aligned with the projected profile of the distal end of the shaft. The projected profile of the distal end of the shaft is shown with dotted lines 215 on FIG. 2b. In this predetermined configuration: the supporting body 213 is not rotated relative to the shaft 202 about the pitch joint 205, and/or the end effector 201 is not rotated relative to the supporting body 213 about the yaw joints 207 and 211, and/or the opening angle of the end effector elements 209, 210 is minimised. The opening angle of the end effector elements 209, 210 may be zero if they abut. In the predetermined configuration, each joint of the articulated coupling 203 may be at the centre of its range of motion. The predetermined configuration of step 602 may be one in which the end effector has a pose relative to the shaft which is different to being most closely aligned with the profile of the distal end of the shaft.

In the predetermined configuration, the roll joint of the instrument shaft may be at the centre of its range of motion. This is implemented by commanding driving forces to drive the roll joint about its axis. This therefore no longer requires the surgeon to actively unroll the instrument manually when the limit of the roll joint is reached. In the predetermined configuration, the roll joint of the instrument shaft may be at one limit of its range of motion, that limit being different to the joint limit reached by repetitive roll motion of the surgeon in the opposite rotational direction. For example, in a suturing operation, if the control system receives information that the suturing operation is to continue, then it may respond to receipt of an input by unrolling the roll joint of the surgical instrument beyond the centre of its range of motion to its other joint limit. This maximises the travel available for continued suturing motion.

Thus, in response to the user actuating the input, the distal end of the instrument may be straightened. The input may be a single input. For the example in which the surgical instrument is being removed from the body, in response to a single input, the surgical instrument is controlled to adopt a straightened configuration which enables it to be retracted through the port. This therefore no longer requires the surgeon to actively straighten each joint of the articulated coupling to the correct degree in order to enable the instrument to be safely retracted through the port.

At step 602, the control system may respond to the command received at step 601 by commanding driving forces to be applied to one or more joints of the robot arm in order to drive the robot arm to adopt a predetermined arm configuration.

For example, the predetermined arm configuration may be one in which the terminal roll joint 305*h* is at the centre of its range of motion. For the example in which the surgical instrument has become rolled up, for example during a suturing operation, in response to an input (which may be a single input), the surgical instrument is unrolled by means of roll joint 305*h* of the robot arm being unrolled. This is implemented by commanding driving forces to drive the roll joint 305*h* only about its axis. This therefore no longer requires the surgeon to actively unroll the instrument manually when the limit of roll joint 305*h* is reached. For a suturing operation, the surgeon can let go of the needle or pass it to another instrument, then actuate the input to cause the instrument to be unrolled, then pick up the needle to continue suturing.

The predetermined arm configuration may be one in which the terminal roll joint 305*h* is at one limit of its range of motion, that limit being different to the joint limit reached by repetitive roll motion of the surgeon in the opposite rotational direction. For example, in a suturing operation, if the control system receives information that the suturing operation is to continue, then it may respond to receipt of an input by unrolling the surgical instrument by means of roll joint 305*h* beyond the centre of its range of motion to its other joint limit. This maximises the travel available for continued suturing motion.

The predetermined configuration may be one in which the drive assembly interface of the robot arm is oriented so as to be facing upwards when the robot is on a horizontal surface. Referring to FIG. 4*c*, the drive assembly interface (which interfaces with the instrument interface) is facing the direction X. This direction X is vertical in the predetermined configuration when the robot is on a horizontal surface. This is implemented by commanding some or all of the robot arm joints to rotate so as to cause the drive assembly interface to be facing the direction X. This makes it easier for the bedside staff to detach/attach an instrument to the robot arm.

The control system may set the predetermined arm configuration to be the configuration of the robot arm at the time that the surgical instrument is attached to the arm before the operation begins. Typically, the bed side staff manoeuvre the arm into a U-shaped (or horseshoe-shaped) configuration at this time, at which none of the robot arm joints is near its joint limits. The control system receives the angular position of each joint from the joint position sensors 308. The control system records the received set of joint positions as the predetermined arm configuration.

The predetermined configuration may be any one or combination of the predetermined configurations described above.

In order to safeguard against misuse of the input to straighten the instrument, the control system may implement any one or combination of the following precautions:

1. The control system may determine if the surgeon has active control of the surgical instrument. Upon receipt of the command at step 601, the control system only proceeds to step 602 if the control system determines that the surgeon has active control of the surgical instrument. The control system may determine that the surgeon has active control of the surgical instrument on determining that a clutch button of the surgeon input device is engaged.

2. The control system may determine if an instrument change mode has been enabled. Upon receipt of the command at step 601, the control system only proceeds to step 602 if the control system determines that an instrument change mode has been enabled. In instrument change mode, after step 601 but prior to step 602, the control system may command the end effector elements 209, 210 to open. This causes the end effector to release tissue it was gripping prior to extraction of the surgical instrument from the surgical site. Then on detecting that the surgical instrument has started to be retracted from the surgical site, the control system proceeds to step 602 to cause the instrument to adopt the predetermined configuration.

3. The control system may wait for a predetermined interval T after receiving the command at step 601 before commanding the driving forces to be applied at step 602. If the input stops being actuated by the user during the time interval T, then the control system does not progress to step 602. T may be in the range 10 ms-1000 ms. T may be 200 ms.

4. The control system may determine if the brake has been applied to the robot arm. Upon receipt of the command at step 601, the control system only proceeds to step 602 if the control system determines that the brake has been applied.

5. The control system only commands driving forces to be applied to cause the instrument to adopt the predetermined configuration at step 602 for the time period in which the user continues to actuate the input at step 601. If the user stops actuating the input, then the control system stops commanding the driving forces of step 602 to be applied.

6. The control system may implement a collision avoidance mechanism. Upon receipt of the command at step 601, the control system only proceeds to step 602 if the control system determines that in implementing step 602, the robot arm will not collide with another structure (such as another robot arm).

7. The control system may implement feature detection/recognition at the surgical site in order to determine if the instrument is safe to move without contacting or disturbing surrounding tissue. Upon receipt of the command at step 601, the control system only proceeds to step 602 if the control system determines that there is sufficient clearance around the instrument end effector to avoid disturbing the surrounding tissue when implementing step 602.

In response to receiving the command from the input at step 601, the control system may compare the current configuration of the instrument to the predetermined configuration. The control system may then only go on to implement step 602 if the current configuration and the predetermined configuration of the instrument differ by more than an instrument tolerance value. Each joint of the instrument may have an individual tolerance value. For example, this individual tolerance value may be in the range 0.005 to 0.02 radians. The individual tolerance value may be 0.01 radians. The opening angle of the end effector elements may also have an individual tolerance value. If any individual joint exceeds its individual tolerance value, or the opening angle exceeds its individual tolerance value, then the current configuration is determined to exceed the predetermined configuration of the instrument by more than the instrument tolerance value. If the current configuration does not differ from the predetermined configuration by more than the instrument tolerance value, then the control system treats the instrument as already having the predetermined configuration, and hence does not go on to implement step 602.

In response to receiving the command from the input at step 601, the control system may compare the current configuration of the robot arm to the predetermined arm configuration. The control system may then only go on to command driving forces to be applied to joint(s) of the robot arm if the current configuration of the robot arm and the predetermined arm configuration differ by more than an arm tolerance value. Only the final roll joint 305*h* of the robot arm may be considered. In other words, the current configuration of the robot arm may only be considered to differ from the predetermined arm configuration by more than the arm tolerance value if the final roll joint 305*h* differs from its predetermined joint position by more than its individual tolerance value. The final roll joint's individual tolerance value may be in the range 0.0005 to 0.01 radians. The final roll joint's individual tolerance value may be 0.001 radians. Alternatively, each joint of the robot arm may have an individual arm tolerance value. In this case, if any individual joint exceeds its individual tolerance value, then the current arm configuration is determined to exceed the predetermined arm configuration by more than the arm tolerance value. If the current arm configuration does not differ from the predetermined arm configuration by more than the arm tolerance value, then the control system treats the arm as already having the predetermined arm configuration, and hence does not go on to command driving forces to be applied to joint(s) of the robot arm to change its configuration to the predetermined arm configuration.

Using the tolerance approach described above prevents the instrument/robot arm being driven to indefinitely oscillate around the predetermined configuration due to a round-off error in the computation.

The control system for implementing the methods described herein may be implemented at the control system 118 as shown in FIG. 1. In this case, the control system 118 receives both inputs from the surgeon's console 112 and inputs from the robot arm 100. In the case that the input of step 601 is located on the robot arm or support structure, the command from this input is sent from the robot arm or support structure to the control system 118. Upon receiving conflicting commands from the surgeon's console 112 and the input, the control system may override the command from the surgeon's console with the command from the input. This may be subject to the control system checking the robot arm state machine and/or the state machine of the whole robotic system.

The control system for implementing the methods described herein may be implemented at the robot arm. For example, in the example in which the input is located on the robot arm, the control system may also be located at the robot arm. The arm control system comprises a processor and a memory. The memory stores, in a non-transient way, software code that can be executed by the processor to cause the processor to control the robot arm and instrument in the manner described herein. The arm control system receives inputs from the control system 118 and also receives the input actuated by the user. The arm control system converts these to control signals to move the joints of the robot arm and/or the joint(s) of the articulated coupling and/or the joint(s) of the end effector. The arm control system may receive conflicting commands from the control system 118 and the input actuated by the user. Upon receiving conflicting commands, the arm control system may override the command from the control system 118 with the command from the input. This may be implemented by the data packets received by the arm control system from the control system 118 comprising a mode field or flags which enable position commands originating from the surgeon's console to be overwritten by the arm control system. A mode field includes information relating to the mode of the robot arm. Example modes are: surgical mode in which the surgeon is controlling the robot arm to perform surgery, and instrument change mode in which the instrument can be safely removed from the robot arm and another instrument attached. This mode information aids the arm control system to prioritise the command from the input over the command from the surgeon's console efficiently, without requiring the arm control system to otherwise retrieve this information from the system state machine.

The control system may be distributed across the robotic surgical system. For example, the control system 118 may perform the method of FIG. 6 with respect to inputs actuated on the surgeon's console, whereas an arm control system may perform the method of FIG. 6 with respect to an input actuated on the robot arm.

The methods described herein enable the instrument to be returned to a nominal straight configuration in a safe manner in which the surgeon retains control of the instrument whilst requiring a reduced effort from the surgeon compared to known methods.

The end effector may take any suitable form. For example, the end effector could be a pair of curved scissors, an electrosurgical instrument such as a pair of monopolar scissors, a needle holder, a pair of jaws, or a fenestrated grasper.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system configured to control manipulation of a surgical instrument in response to manipulation of a remote surgeon input device at a remote surgeon's console, the surgical instrument being supported by a surgical robot arm, the surgical robot arm comprising a series of links between a base and an attachment for the surgical instrument, the links being interspersed by joints of the surgical robot arm, the surgical instrument comprising an end effector connected to a distal end of a shaft by an articulated coupling, the articulated coupling comprising one or more joints of the articulated coupling, the control system configured to:
   receive a command from an input actuated by a user to straighten the surgical instrument; and
   in response to the received command, to:
   (i) command driving forces to be applied to one or more of the one or more joints of the articulated coupling to drive the instrument to adopt a predetermined configuration in which a profile of the end effector is aligned with a projected profile of the distal end of the shaft, and
   (ii) command, independent of driving the instrument to adopt the predetermined configuration, driving forces to be applied to one or more of the joints of the surgical robot arm to drive the surgical robot arm to adopt a predetermined arm configuration.

2. A control system as claimed in claim 1, wherein in the predetermined configuration, each joint of the articulated coupling is at a centre of a range of motion of the respective joint of the articulated coupling.

3. A control system as claimed in claim 1, wherein the articulated coupling comprises a pitch joint and two yaw joints.

4. A control system as claimed in claim 1, wherein the end effector comprises a pair of opposable end effector elements separated by an opening angle, wherein in the predetermined configuration, the opening angle is minimised.

5. A control system as claimed in claim 1, wherein the surgical robot arm comprises a terminal joint adjacent to the attachment for the surgical instrument, that terminal joint being a roll joint, wherein in response to the received command, the control system is configured to command a driving force to be applied to the roll joint to drive the roll joint to a centre of a range of motion of the roll joint.

6. A control system as claimed in claim 1, wherein in the predetermined arm configuration, the attachment for the surgical instrument is oriented such that the surgical instrument can be attached and/or removed vertically from the attachment for the surgical instrument when the surgical robot arm is on a horizontal surface.

7. A control system as claimed in claim 1, wherein the predetermined arm configuration matches a configuration of the robot arm whilst the surgical instrument was being attached to the attachment for the surgical instrument.

8. A control system as claimed in claim 1, configured to, on receiving the command from the input, wait for a predetermined time before responding by commanding driving forces to be applied to the articulated coupling and/or robot arm joints.

9. A control system as claimed in claim 1, configured to, on receiving the command from the input, measure the current configuration of the surgical instrument, and only command driving forces to be applied to joint(s) of the articulated coupling if the current configuration of the surgical instrument differs from the predetermined configuration by greater than an instrument tolerance value.

10. A control system as claimed in claim 1, configured to, on receiving the command from the input, measure the current configuration of the robot arm, and only command driving forces to be applied to joint(s) of the surgical robot arm if the current configuration of the robot arm differs from the predetermined arm configuration by greater than an arm tolerance value.

11. A control system as claimed in claim 1, wherein the input is part of the remote surgeon's console.

12. A control system as claimed in claim 11, wherein the input is located on a hand controller of the remote surgeon's console, the input able to be actuated by motion of the user's hand.

13. A control system as claimed in claim 11, wherein the input is a voice sensor able to be actuated by the user's voice.

14. A control system as claimed in claim 13, wherein the input is a combined input located on two hand controllers of the remote surgeon's console, the combined input able to be actuated by motion of both of the user's hands.

15. A control system as claimed in claim 11, configured to, on receiving the command:
   determine if the surgeon has active control of the surgical instrument; and
   only if the surgeon has active control of the surgical instrument, respond to the received command by commanding driving forces to be applied to joint(s) of the articulated coupling.

16. A control system as claimed in claim 1, wherein the input is on the surgical robot arm.

17. A control system as claimed in claim 15, configured to, on receiving the command:
   determine if an instrument change mode has been enabled; and
   only if the instrument change mode has been enabled, respond to the received command by commanding driving forces to be applied to joint(s) of the articulated coupling.

18. A control system as claimed in claim 1, configured to only command driving forces to be applied to joint(s) of the articulated coupling and/or robot arm joints whilst the input is being actuated by the user.

19. A control system as claimed in claim 16, configured to:
   receive the command from the input on the surgical robot arm;
   receive another command from an input on the remote surgeon input device, the other command to manipulate the surgical instrument; and
   override the other command with the command from the input on the surgical robot arm.

* * * * *